US008666116B2

(12) United States Patent
Kirenko et al.

(10) Patent No.: US 8,666,116 B2
(45) Date of Patent: Mar. 4, 2014

(54) METHOD AND SYSTEM FOR OBTAINING A FIRST SIGNAL FOR ANALYSIS TO CHARACTERIZE AT LEAST ONE PERIODIC COMPONENT THEREOF

(75) Inventors: Ihor Olehovych Kirenko, Eindhoven (NL); Vincent Jeanne, Eindhoven (NL); Gerard De Haan, Eindhoven (NL); Adriaan Johan Van Leest, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 20 days.

(21) Appl. No.: 13/500,000

(22) PCT Filed: Sep. 29, 2010

(86) PCT No.: PCT/IB2010/054396
§ 371 (c)(1),
(2), (4) Date: Apr. 3, 2012

(87) PCT Pub. No.: WO2011/042839
PCT Pub. Date: Apr. 14, 2011

(65) Prior Publication Data
US 2012/0195486 A1    Aug. 2, 2012

(30) Foreign Application Priority Data

Oct. 6, 2009    (EP) .................................... 09172337

(51) Int. Cl.
*G06K 9/00*    (2006.01)
(52) U.S. Cl.
USPC .......................................... 382/103; 382/128
(58) Field of Classification Search
None
See application file for complete search history.

(56) References Cited

U.S. PATENT DOCUMENTS

| | | | |
|---|---|---|---|
| 5,719,950 A * | 2/1998 | Osten et al. | 382/115 |
| 2003/0163032 A1 | 8/2003 | Terry | |
| 2005/0058456 A1 | 3/2005 | Yoo | |

(Continued)

FOREIGN PATENT DOCUMENTS

WO    2010100594 A2    9/2010

OTHER PUBLICATIONS

Viola et al: "Robust Real-Time Object Detection"; Proceedings of IEEE Second International Workshop on Statistical and Computational Theories of Vision-Modeling, Learning, Computing, and Sampling, Vancouver, Canada, Jul. 2001, 25 Page Article.

(Continued)

*Primary Examiner* — Bhavesh Mehta
*Assistant Examiner* — Siamak Harandi (57) ABSTRACT

A method of facilitating obtaining a first signal, for analysis to characterize at least one periodic component, includes obtaining two second signals representative of intensities of electromagnetic radiation. The first signal is at least derivable from an output signal obtainable by applying a transformation to the second signals such that any value of the output signal is based on values from each respective second signal at corresponding points in time. The method further includes obtaining a value of a variable determining influences of components of respective second signals on the output signal when the signals corresponding to the second signals are captured and the transformation is applied, by (i) analyzing the first, second and/or the output signals to select a value of a parameter corresponding to a respective one of the variables; or (ii) calculating values of at least one time-varying factor corresponding to a respective one of the variables.

14 Claims, 6 Drawing Sheets

(56) References Cited

U.S. PATENT DOCUMENTS

| | | | |
|---|---|---|---|
| 2007/0024946 | A1 | 2/2007 | Panasyuk et al. |
| 2008/0273768 | A1 | 11/2008 | Dennis et al. |
| 2009/0018409 | A1 | 1/2009 | Banet et al. |
| 2009/0045847 | A1 | 2/2009 | Lin et al. |
| 2009/0141124 | A1 | 6/2009 | Liu et al. |
| 2011/0251493 | A1* | 10/2011 | Poh et al. ............ 600/477 |

OTHER PUBLICATIONS

Takano et al:"Heart Rate Measurement Based on a Time-Lapse Image"; Science Direct, Medical Engineering & Physics, vol. 29., 2007, pp. 853-857.

Verkruysse et al: "Remote Plethysmographic Imaging Using Ambient Light"; Optics Expressm Dec. 2008, vol. 16, No. 26, pp. 21434-21445.

Yang et al: "Vital Sign Estimation From Passive Thermal Video"; IEEE Confernece on Computer Vision and Pattern Recognition, 2008, CVPR, Jun. 2008, pp. 1-8.

Mohan et al: "Contact-Less, Multi-Spectral Imaging of Dermal Perfusion"; IEEE Instrumentation and Measurement Technology Conference, May 2008, Vancouver Island, Canada, pp. 793-796.

Wieringa et al: "Contactless Multiple Wavelength Photoplethysmographic Imaging: A First Step Toward "SpO2 Camera" Technology"; Annals of Biomedical Engineering, Aug. 2005, vol. 33, No. 8, pp. 1034-1041.

Hu et al: "Feasibility of Imaging Photoplethysmography"; IEEE International Conference on Biomedial Engineering and Informatics, May 2008, pp. 72-75.

Viola et al: "Robust Real-Time Face Detection"; International Journal of Computer Vision, vol. 57, No. 2, pp. 137-154, 2004.

De Haan et al: "True-Motion Estimation With 3-D Recursive Search Block Matching"; IEEE Transactions on Circuits and Systems for Video Technology, vol. 3, No. 5, Oct. 1993, pp. 368-379.

* cited by examiner

METHOD AND SYSTEM FOR OBTAINING A FIRST SIGNAL FOR ANALYSIS TO CHARACTERIZE AT LEAST ONE PERIODIC COMPONENT THEREOF

FIELD OF THE INVENTION

The invention relates to a method of facilitating obtaining a first signal for analysis to characterize at least one periodic component thereof.

The invention also relates to a system for obtaining a first signal for analysis to characterize at least one periodic component thereof.

The invention also relates to a computer program.

BACKGROUND OF THE INVENTION

European patent application No. 09154493.2, in the name of the same applicant as the present application, was filed before and published after the priority date of the present application. It describes a system arranged to process a sequence of images. The system carries out this processing in order to determine at least one of the presence and a frequency value of at least one peak in the spectrum of a signal based on the pixel data of the images corresponding to a frequency of a periodic physiological phenomenon. An image segmentation algorithm is performed on at least one of the sequence of images. One or more distinct segments determined to correspond to a body part of a desired type are tracked through the sequence of images. For each selected and tracked segment a measurement zone is selected. For each measurement zone, a signal representative of the time-varying average brightness of the pixels corresponding to the measurement zone is generated. The brightness may be a weighted sum of the color components or only the value of one color component. The signal is centered on its mean value, and basic signal processing techniques are used to determine one or more local maxima of the spectrum of the signal, at least within a range known to comprise typical heart rate values and/or respiration rate values for the living beings of interest (generally humans).

SUMMARY OF THE INVENTION

It is desirable to provide a method, system and computer program for facilitating obtaining a first signal for analysis to characterize at least one periodic component thereof in which the components of interest are relatively clearly distinguished from noise, for example noise due to motion and illumination changes.

To this end, the invention proposes a method of facilitating obtaining a first signal for analysis to characterize at least one periodic component thereof, including:

obtaining at least two second signals representative of intensities of captured electromagnetic radiation, each corresponding to a respective different radiation frequency range, the first signal being at least derivable from an output signal obtainable by applying a transformation to the second signals such that any value of the output signal is based on values from each respective second signal at corresponding points in time, the method further including:

obtaining at least one value of at least one variable determining influences of at least components of respective second signal on the output signal when the signals corresponding to the second signals are captured and the transformation is applied, by at least one of:

(i) analyzing at least one of the second signals, an output signal obtained by applying the transformation to the second signals and a first signal derived from the output signal and using the analysis to select at least one value of at least one parameter corresponding to a respective one of the variables; and (ii) calculating values of at least one time-varying factor corresponding to a respective one of the variables, each factor value based on at least one second signal value, and applying each factor in an operation in at least one of a number of parallel sequences of operations comprising at least one such operation and taking a signal corresponding to a respective one of the second signals as input.

The method is suitable for facilitating a method in which reflected, transmitted or radiated light is captured and processed to obtain a signal representative of at least variations in a value based on intensity values in the different frequency ranges, also referred to here as color channels. This signal is analyzed to characterize certain periodic phenomena in the scene from which the reflected, transmitted and/or emitted light is captured. Because certain color channels exhibit weaker variations due to the phenomenon of interest than others, whereas motion and illumination changes influence each of the second signals, the transformation applied to the second signals is suitable for obtaining an output signal with an increased signal-to-noise ratio. However, simply subtracting one of the second signals from another will generally not be sufficient to remove the influence of motion and illumination changes. By analyzing at least one of the second signals, the output signal and the first signal and using the analysis to select at least one value of at least one parameter determining influences of at least components of respective second signals on the output signal when the signals corresponding to the second signals are captured and the transformation is applied, it is established whether and to what extent each color channel should influence the output signal and thus the first signal. The respective parameter values affect fewer than all of the second signals that are used to obtain the output signal. They may in particular affect the extent to which the second signals influence the output signal, i.e. the relative strength of the second signals affected by the parameter values in the mix of second signals used to obtain the output signal. Compared to methods that subtract an intensity signal obtained at one wavelength from one obtained at another, or to those that take a ratio, the present method works well with second signals that each contain a component associated with the periodic phenomenon of interest to at least a limited extent. The relevant information from multiple channels is used, whilst at the same time unwanted information is suppressed.

This is also the case where values of at least one time-varying factor are calculated and each factor value is based on at least one second signal value, because a kind or normalization is achieved. By applying the factors to signals based on respective ones of the second signals, a transformation, in particular a kind of normalization, in color space is obtained. Because the factor is time-varying, changes in the background illumination spectrum can be removed, improving the signal-to-noise ratio. The signals obtained by applying the factors can be combined subsequently into one signal from which the first signal is at least derivable, which is implied by the fact that the factors are variables determining influences of at least components of respective second signals on the output signal when the transformation is applied. In this respect, the method differs from those that simply take a ratio of color components and characterize a periodic component of that ratio. It is observed that the signals based on respective ones of the second signals each correspond to a respective one of the second signals, a scalar multiple thereof, or a signal obtainable by applying another of the factors to one of the second signals. Thus, where the values of at least one time-varying factor are calculated, each second signal forms the input to a respective sequence of one or more operations in which the calculated factors are applied. The outputs are then combined into an output signal from which the first signal is at least derivable.

In an embodiment, the analysis of at least one of the second signals, an output signal obtained by applying the transformation to the second signals and a first signal derived from the output signal is used to select at least one value of at least one parameter determining influences of at least components of respective second signals on the output signal so as to maximize a relative signal strength in a limited part of a spectrum of the first signal.

Thus, where it is known a priori that a particular range of the total spectrum of the first signal comprises the information associated with the phenomenon of interest, the method improves the signal-to-noise ratio in that range.

In an embodiment, the transformation includes at least one parameterized operation and the analysis of at least one of the second signals, an output signal obtained by applying the transformation to the second signals and a first signal derived from the output signal is used to select values of at least one parameter of the operation.

Compared to selecting parameters affecting the illumination of a scene, this embodiment is relatively certain to lead to good results. Moreover, it is less obtrusive than changing the lighting conditions.

In a variant, the operation is an operation taking at least two inputs based in different ways on the second signals.

The inputs can simply correspond to values comprised in different respective second signals, or one can be a sum and the other a difference, for example. This embodiment enables the two inputs to be combined in such a way that the parameter values determine, for example, multiplication factors or phase changes applied to the inputs being combined.

In a further variant, the transformation includes an operation carried out in parallel on respective input signals using at least one parameter value specific to fewer than all of the input signals.

Thus, an alternative way of affecting the prominence of the different second signals in the output signal is provided.

In a further variant, the transformation includes at least one parameterized non-linear operation and the analysis of at least one of the second signals, an output signal obtained by applying the transformation to the second signals and a first signal derived from the output signal is used to select values of at least one parameter of the operation.

Thus, the influence of a particular color channel on the output signal of the transformation can be made dependent on amplitude and/or frequency. This variant can, for example, be used to allow large-signal fluctuations in one color channel to influence the output signal but not small-signal fluctuations, or vice versa.

In an embodiment, the transformation includes an operation carried out in parallel on respective input signals, each a different linear combination of second signals with at least one coefficient differing from zero, the operation comprising taking a logarithm of the input signal.

Generally, the operation will be carried out on respective input signals that are scalar multiples of the second signals or correspond to the second signals.

Variations in ambient illumination levels will in many situations affect each color channel to approximately the same degree. In essence, each second signal is the result of a modulation by a signal representative of variations in ambient illumination levels. The output of the logarithm is a signal that has an additive component related to the multiplicative variations in ambient illumination levels. One can think of the output as the sum of a signal representative of variations in ambient illumination levels and a signal that is independent thereof and includes a component representative of a periodic phenomenon of interest. The latter signal is generally different for each color channel, because each color channel is affected differently by the periodic phenomenon. The signal representative of variations in ambient illumination levels can be suppressed relatively easily. One way of doing this is by means of a subsequent operation projecting onto a plane in a multidimensional space input signals at least derived from respective output signals of the operation that comprises the taking of the logarithm. This multidimensional space will generally have a number of dimensions equal to the number of second signals (e.g. three, where the second signals represent red, green and blue color channels). The multidimensional space can be thought of as a color space. It is noted that variations due to movement of a region of interest that is imperfectly tracked will result in similar effects as variations in ambient illumination levels, which effects are similarly suppressed in this embodiment.

In an embodiment, each second signal comprises a sequence of image frames comprised of pixel values representative of intensities of captured electromagnetic radiation in an associated radiation frequency range.

This embodiment is relatively easy to implement using a video camera, because such a camera already comprises filters to provide image frames in multiple color channels. Moreover, random noise can be reduced by combining pixel values from different locations in the image to form the first signal or a precursor thereof.

In an embodiment, the second signals include a second signal comprising intensity values of captured electromagnetic radiation in a part of the electromagnetic spectrum tuned to a peak in an absorption spectrum of water.

This embodiment is suitable for facilitating obtaining a first signal for analysis to characterize at least one periodic component thereof corresponding to a biological phenomenon in a living being from whom radiated, reflected or transmitted light is captured.

In particular, this variant can be used to facilitate the implementation of a photoplethysmographic method for determining the heart rate of the living being.

In an embodiment, the second signals include a second signal comprising intensity values of captured electromagnetic radiation in a part of the electromagnetic spectrum corresponding to a range of wavelength values between 500 nm and 600 nm.

This embodiment is similarly suitable for facilitating obtaining a first signal for analysis to characterize at least one periodic component thereof corresponding to a biological phenomenon in a living being from whom radiated, reflected or transmitted light is captured. The second signal comprising intensity values of captured electromagnetic radiation in a part of the electromagnetic spectrum corresponding to a range of wavelength values between 500 nm and 600 nm will contain information about changes in the level of oxyhemoglobin in illuminated (skin) tissue.

In an embodiment, the analysis includes carrying out a principal component analysis on data sets respectively based on a plurality of second signals.

This embodiment provides a suitable implementation of the analysis step of the general method where one second signal is relatively strongly correlated with the periodic phenomenon of interest and the other signal relatively weakly. The signals can be subjected to a matrix operation to obtain an output signal on which the first signal is based, in particular to which it corresponds. The parameters of the matrix operation are derived from the principal components. Carrying out a principal component analysis on the second signals allows one to determine the correlations between the second signals. One of the principal components will correspond to the signal component representative of the periodic phenomenon of interest. The matrix operation including parameters based on the principal component analysis is set up such as to retrieve this principal component as the first signal or to retrieve a signal from which the first signal is directly obtainable.

An embodiment, wherein at least one of the second signals, an output signal obtained by applying the transformation to the second signals and a first signal derived from the output signal is analyzed and the analysis is used to select at least one value of at least one parameter determining influences of at least components or respective second signals on the output signal when the signals corresponding to the second signals are captured and the transformation is applied, further includes causing the selected values of the at least one parameter to be loaded into a system comprising:

an interface for obtaining at least two second signals representative of intensities of captured electromagnetic radiation, each corresponding to a respective different radiation frequency range; and a signal processing system for applying a transformation to the second signals to obtain an output signal from which the first signal is at least derivable, any value of the output signal being based on values from each respective second signal at a common point in time, wherein the system is arranged to cause influences of respective second signals on the output signal to be determined at least partly in accordance with the loaded values of the at least one parameter.

This embodiment is thus used to find appropriate parameter values for use in systems manufactured to carry out a method of obtaining the first signal by obtaining at least two second signals representative of intensities of captured electromagnetic radiation, each corresponding to a respective different radiation frequency range, and applying the transformation to the second signals produces an output signal of which any value is based on values from each respective second signal at corresponding points in time.

In an embodiment, the analysis and the selection of at least one parameter value is carried out continually whilst processing the second signals to obtain the first signal.

Thus, this embodiment provides a method that continually adapts to ensure that a first signal is provided in which the periodic component of interest is relatively clearly defined.

In an embodiment, the at least one time-varying factor includes a factor obtainable by calculating a linear combination of corresponding values from each of at least one of the second signals, and the same value of that factor is used in each of the parallel sequences of operations.

An effect of this embodiment is to carry out a normalization with respect to illumination variations unrelated to the periodic phenomenon of interest. Because the signals in the different color channels (the second signals) are affected to essentially the same degree by such variations, any linear combination will result in at least a degree of removal of the modulation due to the illumination variations.

In a variant of this embodiment, the parameters corresponding to a respective one of the variables determining influences of at least components of respective second signals on the output signal when the signals corresponding to the second signals are captured and the transformation is applied include at least one coefficient of the linear combination.

In this embodiment, the factor can be given a value that results in a transformation to a plane in color space that is generally parallel to a line in color space that corresponds to variations due to the periodic phenomenon of interest. For example, in the case of remote photoplethysmography, pulsating blood flow due to the heartbeat and/or respiration of a subject represented in a sequence of color images will cause variations in the color of exposed skin of the subject. In the absence of noise due to other causes of color changes in the images, these variations are along a line in color space. The projection onto a parallel plane will tend to remove the variations due to the other causes.

In a variant in which each second signal comprises a sequence of image frames comprised of pixel values representative of intensities of captured electromagnetic radiation in an associated frequency range, the operations in the parallel sequences are carried out per pixel, with a factor value calculated for each pixel position.

In another embodiment of the method, for at least one of the factors, separate values at corresponding associated points in time are calculated for each of the parallel sequences, each obtained from multiple values of the second signal taken as input by the sequence concerned, the multiple values being associated with respective points in time spanning an interval including the point in time associated with the factor value.

An effect is to carry out a color normalization. Because the factor values are each obtained from multiple values of the second signal taken as input by the second sequence concerned, the multiple values being associated with respective points in time spanning an interval including the point in time associated with the factor value, the relatively slowly varying background color changes can be removed. Those associated with the phenomenon of interest, e.g. pulsating blood flow of a subject represented in image signals corresponding to the second signals, remain.

In a variant of this embodiment, calculating the factor value includes calculating an average of second signal values associated with at least two points in time.

Averaging removes the influence of variations.

In a further variant, the second signals are discrete in time, and the calculation of each factor value includes taking an average of second signal values associated with at least two points in time, of which one corresponds to a point in time associated with the factor value.

The point in time associated with the factor value is the point in time associated with the signal value to which factor value is applied in the relevant operation in the sequence of operations. An effect of this variant is to ensure that the average as closely approximates an instantaneous average value as possible, so that faster background variations can be removed more accurately.

According to another aspect, the system for obtaining a first signal for analysis to characterize at least one periodic component thereof according to the invention includes: an interface for obtaining at least two second signals representative of intensities of captured electromagnetic radiation, each corresponding to a respective different radiation frequency range, the first signal being at least derivable from an output signal obtainable by applying a transformation to the second signals such that any value of the output signal is based on values from each respective second signal at corresponding points in time, wherein the system is arranged to obtain at least one value of at least one variable determining influences of at least components of respective second signals on the output signal when the signals corresponding to the second signals are captured and the transformation is applied, by at least one of:

(i) analyzing at least one of the second signals, the output signal and the first signal and using the analysis to select at least one value of at least one parameter corresponding to a respective one of the variables; and (ii) calculating values of at least one time-varying factor corresponding to a respective one of the variables, each factor value base on at least one second signal value, and applying each factor in an operation in at least one of a number of parallel sequences of operations comprising at least one such operation and taking a signal corresponding to a respective one of the second signals as input.

In an embodiment, the system is configured to carry out a method according to the invention.

According to another aspect of the invention, there is provided a computer program including a set of instructions capable, when incorporated in a machine-readable medium, of causing a system having information processing capabilities to perform a method according to the invention.

BRIEF DESCRIPTION OF THE DRAWINGS

The invention will be explained in further detail with reference to the accompanying drawings, in which.

DETAILED DESCRIPTION OF THE EMBODIMENTS

Figure 1:
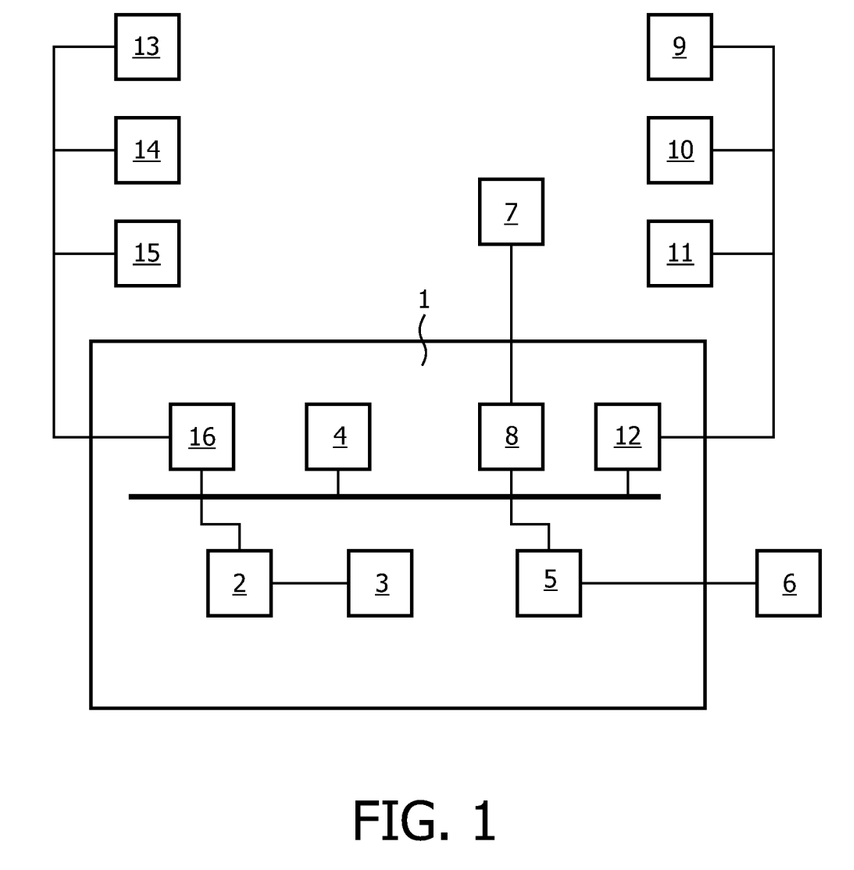
FIG. 1 is a block diagram of a system for extracting information from a signal obtained by applying a transformation to at least two second signals representative of intensities of captured electromagnetic radiation, each corresponding to a respective different radiation frequency range.

A system for carrying out remote photoplethysmography is illustrated by way of example in FIG. 1. Photoplethysmographic imaging is based on the principle that temporal variations in blood volume under the skin lead to variations in light absorption by the skin. Such variations can be detected and measured by taking images of an area of skin and calculating the pixel average over a selected region. They can also be detected by illuminating a selected area of skin with light and measuring the intensity of reflected light with a photosensor. In the example used herein, the system of FIG. 1 is arranged to determine the value of the heart rate of a living being. However, the same system can be used to characterize the phase and/or frequency of some other periodic biological phenomenon, e.g. the respiration rate or oxygenation level.

It is noted that the system illustrated in FIG. 1 and the principles to be explained below can also be used to acquire non-biological temporally vibrating or pulsating signals from images. Examples of suitable applications include the monitoring of industrial equipment and processes to predict impending failure by analyzing vibrations and remote detection of the number of revolutions per second of the engine in a motor vehicle to determine its speed. In all these examples, as in the example to be explained in detail herein, a method is used that is robust to changes in illumination and to motion unrelated to the periodic phenomenon to be analyzed.

In the illustrated embodiment, the system includes a data processing system 1, which can be a general-purpose computer provided with appropriate interfaces or a dedicated device. The data processing system 1 includes a data processing device 2 and main memory 3, as well as a mass-storage device 4. It further includes at least an interface 5 to an output device 6.

The data processing system 1 of the example is arranged to acquire a sequence of images from a video camera 7 via an interface 8. More exactly, the data processing system 1 is arranged to receive a plurality of sequences of image frames in respective color channels. The images frames in a particular color channel comprise pixel values representative of intensities of captured electromagnetic radiation in a particular range of the electromagnetic spectrum. This is due to color filters comprised in the video camera 7.

The sequences of image frames in the different color channels are generally synchronized, in the sense that one image frame from each channel is associated with a particular point in time. If the video camera 7 has only one photosensor array, there will be a slight shift in time between the associated image frames, but the shift will be an order of magnitude smaller than that corresponding to the frequency with which complete images are captured. Generally, however, the video camera 7 will have multiple photosensor arrays, so that the image frames can be captured simultaneously. In an alternative embodiment, multiple video cameras are used.

It is noted that the system can also use photosensors 9-11 with appropriate filters to obtain signals representative of intensities of captured electromagnetic radiation, each corresponding to a respective different frequency range. The signals from the photosensors 9,10,11 are received by the data processing system 1 through an interface 12. In one variant of such an embodiment, a first sensor 9 is arranged to capture red light, a second sensor 10 blue light and a third sensor 11 green light. In an alternative embodiment, one of the sensors 9-11 is arranged to capture a signal (analogue or digital) comprising intensity values of captured electromagnetic radiation in a part of the electromagnetic radiation spectrum corresponding to a wavelength in air in only a range comprised in a range between 500 nm and 600 nm. This corresponds to the green part of the visible spectrum.

In the same or another embodiment, one of the sensors 9-11 is tuned to a frequency corresponding to a peak in the absorption spectrum of water. Suitable frequencies in the visible part of the spectrum are those corresponding to a wavelength in air of 514, 606, 660 or 739 nm. In an alternative variant, one of the sensors 9-11 is tuned to a frequency just outside the visible part of the spectrum (that is in the near infra-red). In particular, the sensor can be tuned to a frequency corresponding to a wavelength in air of 836 nm or 970 nm. Silicon photosensors are particularly sensitive to radiation in the range between 800 and 1000 nm, so that such an embodiment results in a strong captured signal. Silicon photosensors are relatively cheap and common. Although both the video camera 7 and the photosensors 9-11 are shown in FIG. 1, it will be understood that the system can generally use only one of these modalities for capturing signals representative of intensities of captured electromagnetic radiation corresponding to different respective radiation frequency ranges. The present description will proceed on the basis of the embodiment using the video camera 7.

In one embodiment, a standard video camera 7 with Red, Green and Blue channels is used. In another embodiment, the channels can be Cyan, Yellow and Magenta.

One embodiment uses an adapted video camera 7 with a filter that admits light within only a limited range comprised in the range of frequencies corresponding to wavelengths in air of between 500 nm and 600 nm. This means that image frames in this channel comprise pixel values corresponding to captured intensities of green light.

Another embodiment comprises an adapted video camera 7 with a filter tuned to a peak in the absorption spectrum of water. In particular, the filter may be tuned to a frequency corresponding to a wavelength in air of 514, 606, 660 or 739 nm. Where it is desirable to use the system of FIG. 1 in relatively dark situations, the filter can be tuned to a frequency just outside the visible part of the spectrum (that is in the near infra-red). In particular, the sensor can be tuned to a frequency corresponding to a wavelength in air of 836 nm or 970 nm. This has the effect that a video camera 7 with a conventional CMOS or CCD array can be used. Such sensors are particularly sensitive to radiation in the range between 800 and 1000 nm, so that such an embodiment results in a strong captured signal. When used to capture images of one or more living beings, the pixel values in this channel vary relatively strongly with blood plasma flow. It is thus possible to extract a first signal with a relatively strong component having a frequency corresponding the living being's heart rate, as will be explained.

In the illustrated embodiment, the system of FIG. 1 is provided with an (optional) set of light sources 13-15, each tuned to a particular frequency range. In an embodiment, the light sources 13-15 are tuned to frequencies or frequency ranges corresponding to those of the channels of the video camera 7. The data processing system 1 is configured to control the intensities of light emitted in the respective frequency ranges by means of an appropriate interface 16. In an further embodiment, the data processing system 1 the light sources 13-15 are tunable, and the data processing system 1 is arranged to select appropriate parameter values controlling the range of the electromagnetic spectrum within which the light sources 13-15 emit light. This can be combined with appropriate tunable filters for the video camera 7.

Figure 2:
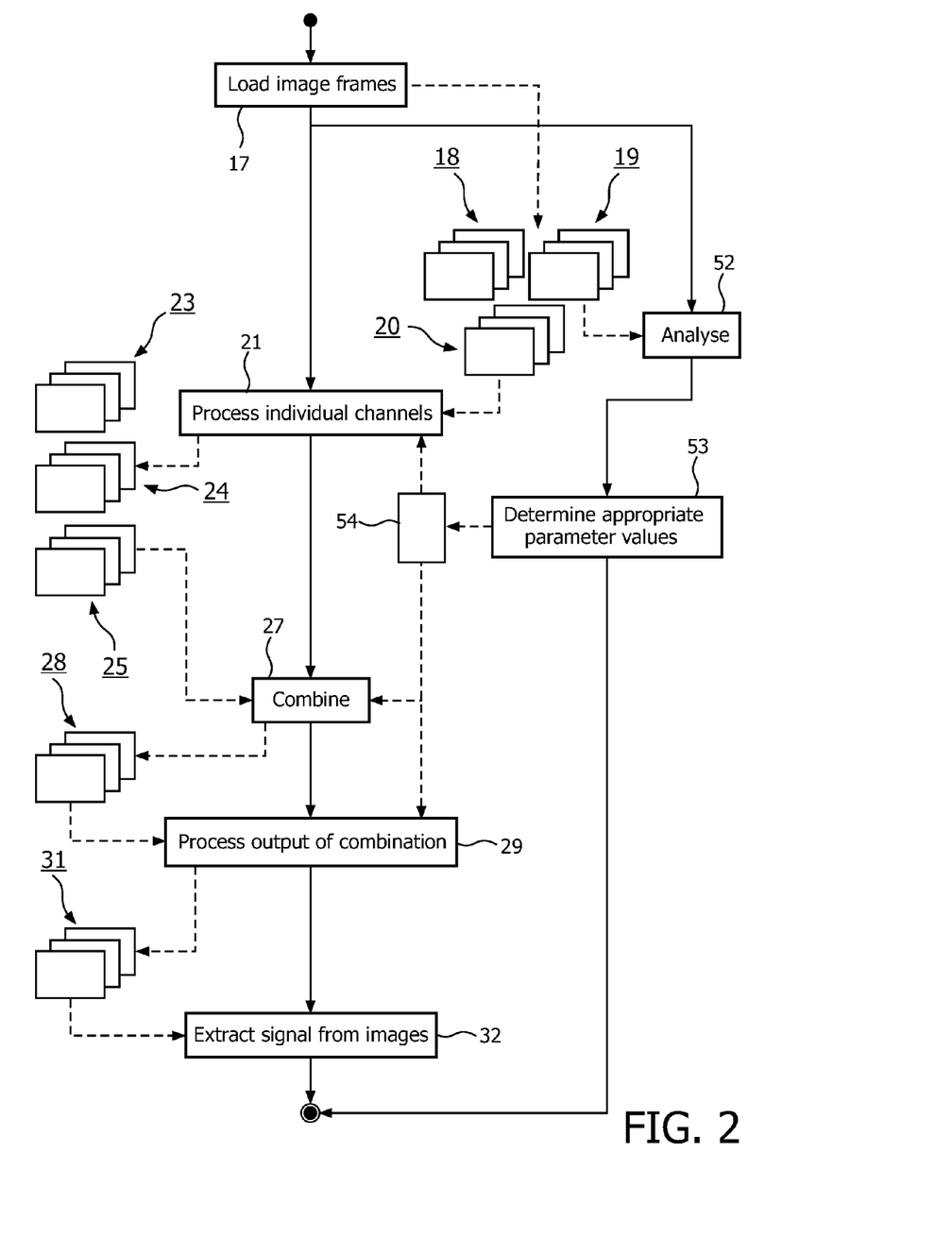
FIG. 2 is a flow chart of a method carried out by the system.

FIG. 2 shows steps in a first method carried out by the data processing system 1 that will be explained also with reference to FIG. 3. In a first step 17, the data processing system 1 loads sequences 18-20 of image frames from each channel. The sequences 18-20 are synchronized in the sense that a particular point in time corresponds to one image frame from each sequence 18-20. Each sequence thus forms a signal, to which a transformation is applied in order to obtain a single output signal. The transformation is of such a nature that each value of the output signal is based on values from each respective second signal at corresponding points in time.

That said, the transformation comprises multiple operations, some of which only take an image frame from one of the sequences 18-20 as input. In the illustrated embodiment, the method includes a step 21 of carrying out an operation 22a-c (FIG. 3) in parallel on one frame from each of the respective sequences 18-20. The operation 22a-c is a parameterized operation 22a-c, meaning that it takes a parameter value as a further input, which parameter value is set separately for each of the respective channels. Generally, it will therefore be different for each of the respective channels. The operation 22a-c can be a non-linear operation, as is illustrated in FIG. 3. An example of several suitable operations is a gamma encoding operation ($V_{out}=V_{in}^\gamma$), with a separate gamma value being used for each channel. The output of this step 21 comprises three parallel sequences 23-25 of individually processed image frames.

A next operation 26 is carried out (step 27) on the sequences 23-25 provided as output in the previous step 21. This operation 26 is an operation taking at least two inputs based in different ways on the sequences 23-25 of individually processed image frames. In the example, the inputs correspond directly to the sequences 23-25. In the example, the operation 26 is a matrix operation. It transforms three image frames into a single image (i.e. an array of values based on pixel values), so that the sequences 23-25 of individually processed image frames are transformed into a single image sequence 28. This step 27 is implemented such that image frames corresponding to a common point in time are used as input.

The output of the matrix operation 26 is subsequently processed (step 29) in a further non-linear operation 30. This can again be a gamma encoding operation. The result is an output sequence 31 of images (i.e. arrays of values based on pixel values). From the output sequence 31, at least one signal is extracted (step 32) for analysis to characterize at least one periodic component thereof. The extracted signal is in the form of a sequence of single values, as opposed to a sequence of arrays of values. Each value is based on multiple pixel values from one image in the output sequence 31.

Figure 3:
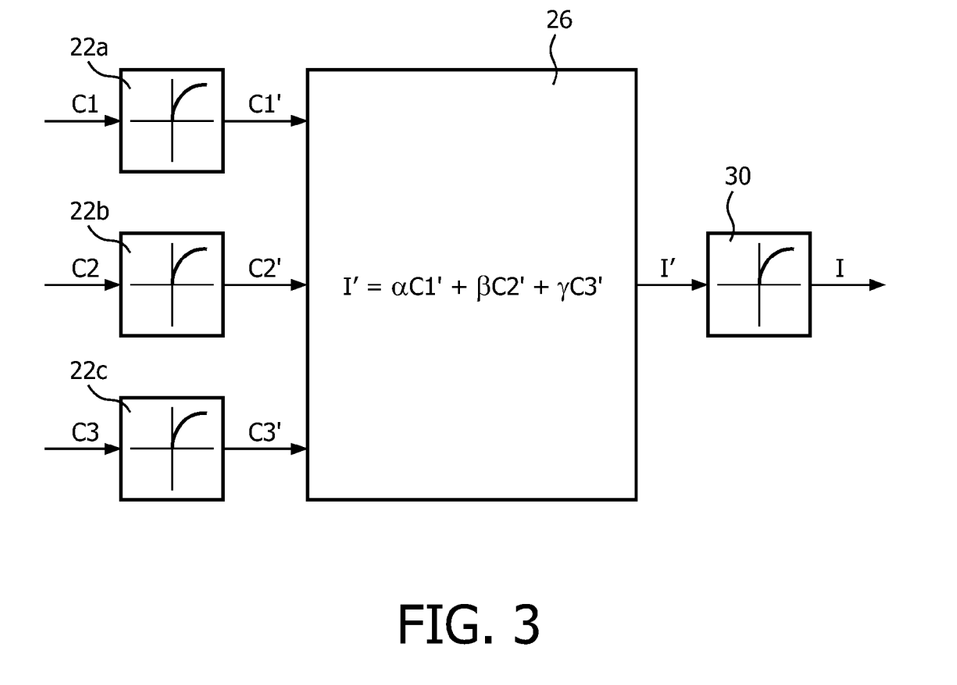
FIG. 3 is a diagram illustrating the transformation applied by the system.

In an alternative implementation of the method illustrated in FIG. 3, the step 21 of carrying out an operation 22a-c (FIG. 3) in parallel on one frame from each of the respective sequences 18-20 does not use a gamma encoding operation. Rather, the operation 22a-c comprises taking the logarithm of the pixel values of the sequences 18-20. In this alternative implementation, the operation 22a-c need not necessarily be parameterized, but it is of course non-linear. Also in this implementation, the output of the step 21 of carrying out the non-linear operation 22a-c in parallel, frame-by-frame on the respective sequences 18-20 comprises three parallel sequences 23-25 of individually processed image frames.

Taking the logarithm is useful for removing signal components due to changes in illumination affecting all the channels. Such changes result from movement of the illuminated subject (e.g. resulting in a shadow falling over an entire region of interest in the frames and/or from changes in background illumination). They are generally multiplicative, in the sense that the signal of interest in each of the channels is multiplied by a modulating factor representative of brightness changes and any changes in the spectrum of the source of illumination. By taking the logarithm, the background illumination becomes additive, making it easier to remove in, for example, the subsequent matrix operation 26. The matrix operation 26 can, for example, involve a projection on a plane in color space that leads to the complete or partial removal of the modulating signal representative of luminance changes. Taking the logarithm does not appreciably affect the signal of interest, i.e. the signal to be extracted from the output sequence 31 of images, because the signal of interest, as will become clear has relatively small variations. Thus, the logarithm approximates to that signal, which will be appreciated by looking at the Taylor expansion of the natural logarithm (ln $z=(z-1)-\frac{1}{2}(z-1)^2+\ldots$).

In a further embodiment (not shown in detail in FIG. 2), the matrix operation 26 is preceded by an operation in which the effects of certain variations in conditions that affect all color channels in a generally equal measure are reduced or eliminated. For example, in remote photoplethysmography, ambient illumination changes, changes in skin transmission and imperfect tracking of regions of interest can lead to modulations of the signals in each of the color channels in the same way. This effect is reduced or removed by dividing each of corresponding pixel values of associated frames of the respective sequences 18-20 by a value that is a linear combination of the pixel values from each of the sequences 18-20. It is noted that embodiments are possible in which all but one of the coefficients of the linear combination are equal to zero.

One can write the sequences 18-20 of image frames in the different respective color channels as follows:

$$\vec{I}(\vec{x}, t) = \begin{bmatrix} R_c(\vec{x}, t) \\ G_c(\vec{x}, t) \\ B_c(\vec{x}, t) \end{bmatrix}, \quad (1)$$

with $\vec{x}$ being the location of a pixel in a frame, and t being a point in time corresponding to a frame in each respective sequence 18-20. The removal or reduction of the effect of luminance variations in the step 21 preceding the matrix operation 26 can then be written as follows:

$$\vec{I}_b(\vec{x}, t) = \frac{1}{\alpha R_c(\vec{x}, t) + \beta G_c(\vec{x}, t) + \gamma B_c(\vec{x}, t)} \vec{I}(\vec{x}, t). \quad (2)$$

It is noted that this is a parameterized operation, and that the values of the coefficients α, β, γ can be optimized by analyzing at least one of the signals represented by the sequences 18-20, the signal resulting from the matrix operation 26 or the signal extracted from the latter signal. However, in general, any set of coefficient values will provide an effect, including a combination in which two of these coefficients have the value zero.

Implementations of the step 32 of extracting at least one signal for analysis to characterize at least one periodic component thereof will now be described.

Figure 4:
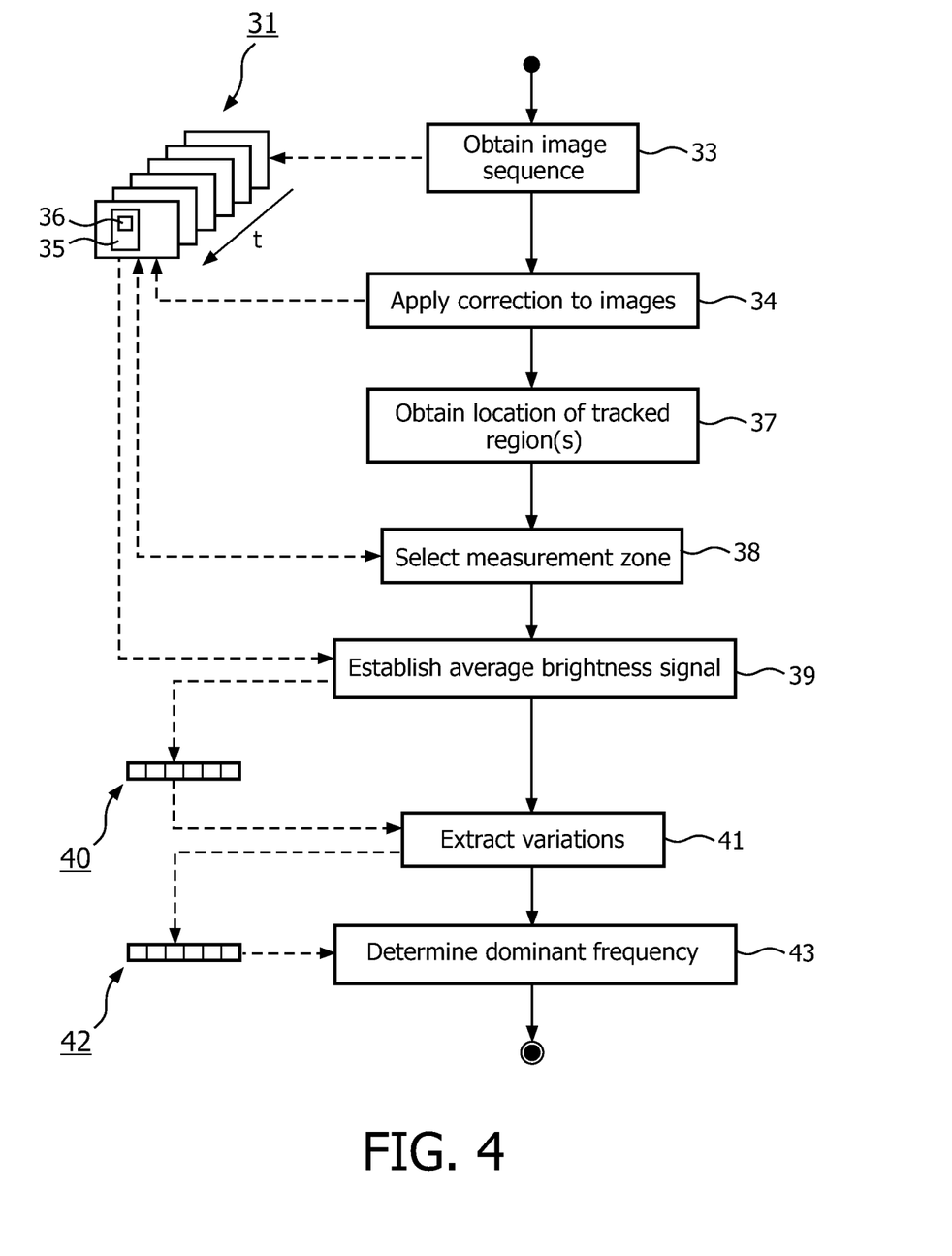
FIG. 4 is a flow chart illustrating some steps carried out by the system to obtain a signal for analysis to characterize at least one periodic component thereof in a first variant.

A first example of an extraction method is illustrated in FIG. 4. Some steps have been omitted for clarity. The order of steps can be varied to a certain extent and certain steps can be carried out at an earlier stage than shown. In particular, certain steps can be carried out at the stage when the image sequences 18,19,20 received from the video camera 7. The illustrated method commences by obtaining (step 33) the output sequence 31 resulting from the last non-linear processing step 29 shown in FIG. 2. In a next step 34, the images are processed to remove non-periodic background signals. In an implementation of this step 34, a correction signal corresponding to the average brightness of part or all of the images in the sequence 31 is formed. The pixel data are then decorrelated from the correction signal. Algorithms for canceling non-linear cross-correlations are known per se. Further image processing can take place in this step 34, e.g. to compensate for camera motion.

In the method of FIG. 4, a region of interest 35 is tracked (step 37) through the sequence 31 of images. The region of interest 35 is selected to correspond to a part of the images representing exposed skin of part of a living being, e.g. the face. A suitable algorithm for selecting such a region of interest 35 is described e.g. in Viola, P. and Jones, M. J., "Robust real-time object detection", *Proc. Of IEEE Workshop on statistical and computational theories of vision*, 13 Jul. 2001. Other techniques can be used instead of or in combination with this technique.

The region of interest 35 is tracked throughout the sequence 31. A suitable tracking algorithm is described in De Haan et al., "True-motion estimation with 3-D recursive search block matching", *IEEE Transactions on circuits and systems for video technology*, 3 (5), October 1993, pp. 368-379. Other tracking algorithms can be used alternatively or in combination with this tracking algorithm.

In the illustrated embodiment, a measurement zone 36 is selected (step 38) within the region of interest 35. The measurement zone 36 is selected by means of a spatial and/or temporal analysis of a plurality of image parts, each one or more image points in size, to determine a set of contiguous parts having similar characteristics. A suitable algorithm is an algorithm for selecting a region with minimal gradient variations. The position of the measurement zone 36 is determined relative to the region of interest 35 in a key image, so that it can subsequently be located in each of the images of the sequence 31.

Next (step 39), values associated with individual image points within the measurement zone 36 are combined for each image, so that a brightness signal 40 is obtained. A suitable combination operation is averaging. This signal 40 is a time-varying signal, since each value corresponds to an image in the sequence 31 and each image in the sequence 31 corresponds to a particular point in time.

This brightness signal 40 is then converted (step 41) into a final signal 42 representative of at least variations in a value based on pixel values from the sequences 18-20 obtained from the video camera 7. In an implementation of this step 41, the brightness signal 40 is centered on its mean value. In a different implementation, this step 41 comprises a filtering operation, e.g. a filtering operation corresponding to differentiation of the average brightness signal 40. Other alternative techniques for extracting variations of the order of 1% of the dynamic range of the brightness signal 40 are also possible.

The final signal 42 is analyzed (step 43) to characterize one or more periodic biological phenomena. In particular, a spectral analysis is used to determine one or more local maxima in its spectrum, at least within a range of frequencies known to comprise typical heart rate values and/or respiration rate values for the living beings of interest (e.g. human beings). In an alternative embodiment, a heart rate extraction method in the time domain is used.

It is observed that a single region of interest 35 and a single measurement zone 36 have been described for illustrative purposes. In other embodiments, multiple regions of interest within the sequence 31 are tracked and/or multiple measurement zones within one region of interest are used to obtain multiple final signals. Clustering algorithms or the like can then be used to arrive at a consensus value for the heart rate, for example.

Figure 5:
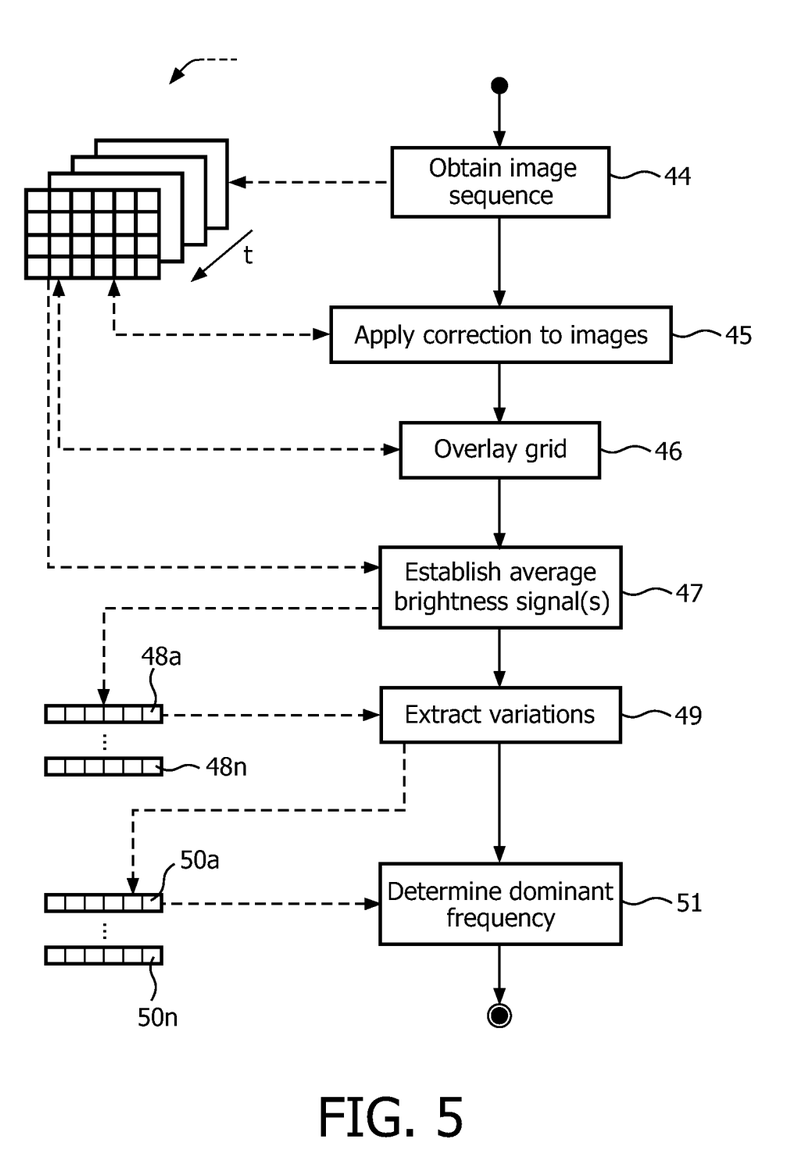
FIG. 5 is a flow chart illustrating some steps in carried out by the system to obtain a signal for analysis to characterize at least one periodic component thereof in a second variant.

FIG. 5 illustrates an alternative method of processing the sequence 31 of images obtained using the method of FIG. 2. Again, certain steps have been omitted for clarity, the order of steps can be changed and certain steps can already be carried out at the stage illustrated in FIG. 2.

Initial steps 44,45 are similar to the first steps 33,34 of the method of FIG. 4. Thus, the sequence 31 of images generated using the method of FIG. 2 is obtained (step 44) and corrected (step 45).

However, in a next step 46, a grid is laid over each of the images in the sequence 31. The grid partitions the images into an array of (potential) measurement zones. Each measurement zone includes a plurality of image points, i.e. pixel locations. Then (step 47), at least one, but generally all of the measurement zones are selected, and, for each measurement zone, a respective signal 48*a-n* corresponding to the time-varying spatial combination of pixel values at image points in the measurement zone concerned is formed. The spatial combination can be an average, mean value or other type of combination. In any case, the value of one of the signals 48*a-n* at a particular point in time is based on multiple pixel values from the image in the sequence 31 corresponding to that point in time. Thus, random noise (as opposed to noise due to camera motion or movement of objects in the represented scene) is cancelled.

Each of the signals 48*a-n* is then centered on its mean value (step 49) to yield a final signal 50*a-n* for analysis to characterize at least one periodic component thereof. Again, instead of centering the signals 48*a-n* on their mean value, a different operation for extracting small-amplitude variations, such as differentiation, can be used.

The analysis of the final signals 50*a-n* is carried out in a last step 51. In this example, the dominant frequency in a particular frequency range is determined. In other applications, a phase map is created for a particular frequency (if a final signal 50*a-n* is created for each measurement zone defined by the grid).

The methods described above with reference to FIGS. 2, 4 and 5 allow for robust continuous monitoring of biometrical signals of people. Moreover, there is minimal interference with the monitored person's daily activities, due to the remote nature of the monitoring. The method can thus be used to provide virtually immediate feedback on a person's mental and physical condition at any instance in time. The method does not require the person being monitored to wear annoying body sensors.

Conventional remote photoplethysmographic methods are limited to remote monitoring of persons within a range of about 1 meter of the video camera 7. Moreover, the subject being monitored should not move, and the illumination should be constant during the acquisition of the video signal.

Steps 52,53 illustrated in FIG. 2 enable the system of FIG. 1 to provide final signals 42,50*a-n* with increased signal-to-noise ratios, at least in as far as the components corresponding to the periodic signals to be analyzed (the components indicative of pulsating blood flow in the example of remote photoplethysmography) are concerned. In particular, the robustness to noise introduced by movement of the video camera 7, movement of the person being monitored and variations in illumination is improved.

To this end, the system analyses (step 52) at least one of the sequences 18-20 of image frames received from the video camera 7, the sequences 23-25 of individually processed image frames, the image sequence 28 resulting from the matrix operation 26, the output sequence 31 of images, the extracted signal 40,48 and the signal 42,50*a-n*, and determines (step 53) appropriate values to provide a set 54 of parameter values for each instance of the first operation 22*a-c*, the matrix operation 26 and the further non-linear transformation operation 30. Alternatively or additionally, parameters for deriving values of control signals determining the relative intensities and/or frequencies of light emitted by the different tuned light sources 13-15 and/or filter coefficients determining the relative attenuations and/or or pass band of light captured by the sensors 9-11 can be included in the set 54 of parameter values.

The parameter values are chosen to optimize the ratio of the wanted signal component (representative of blood volume pulsations) to unwanted signal components (due to illumination changes or motion).

In one embodiment, the data processing system actually calculates the signal-to-noise ratio using the final signals 42,50*a-n* and adjusts the parameter values using an exhaustive or directed search method so as to maximize the calculated signal-to-noise-ratio.

In another embodiment, the data processing system 1 carries out a principal component analysis using only the sequences 18-20 of image frames in the color channels or the individually processed sequences 23-25. Coefficients for the matrix operation are then chosen to be orthogonal to the principal components that are unrelated to the signal component of interest, i.e. the component representative of the heart rate and/or respiration rate.

In the illustrated embodiment, the steps 52,53 are carried out continually whilst the signals represented by the sequences 18-20 are being processed. This embodiment is suitable for situations in which ambient lighting condition change.

In an alternative embodiment, a system as shown in FIG. 1 is used to obtain a set 54 of parameter values for subsequent use in one or more other systems that carry out only the steps 17,21,27,29,32 that result directly in the signals 42,50*a-n* for analysis to characterize at least one periodic component thereof. Thus, a method of manufacturing such other systems includes configuring the systems with the set 54 of parameter values previously obtained using test signals and the full method of FIG. 2. Those systems, like the system carrying out the full method of FIG. 2, are able to extract a signal including a component carrying information representative of a periodic signal that is relatively strong.

Figure 6:
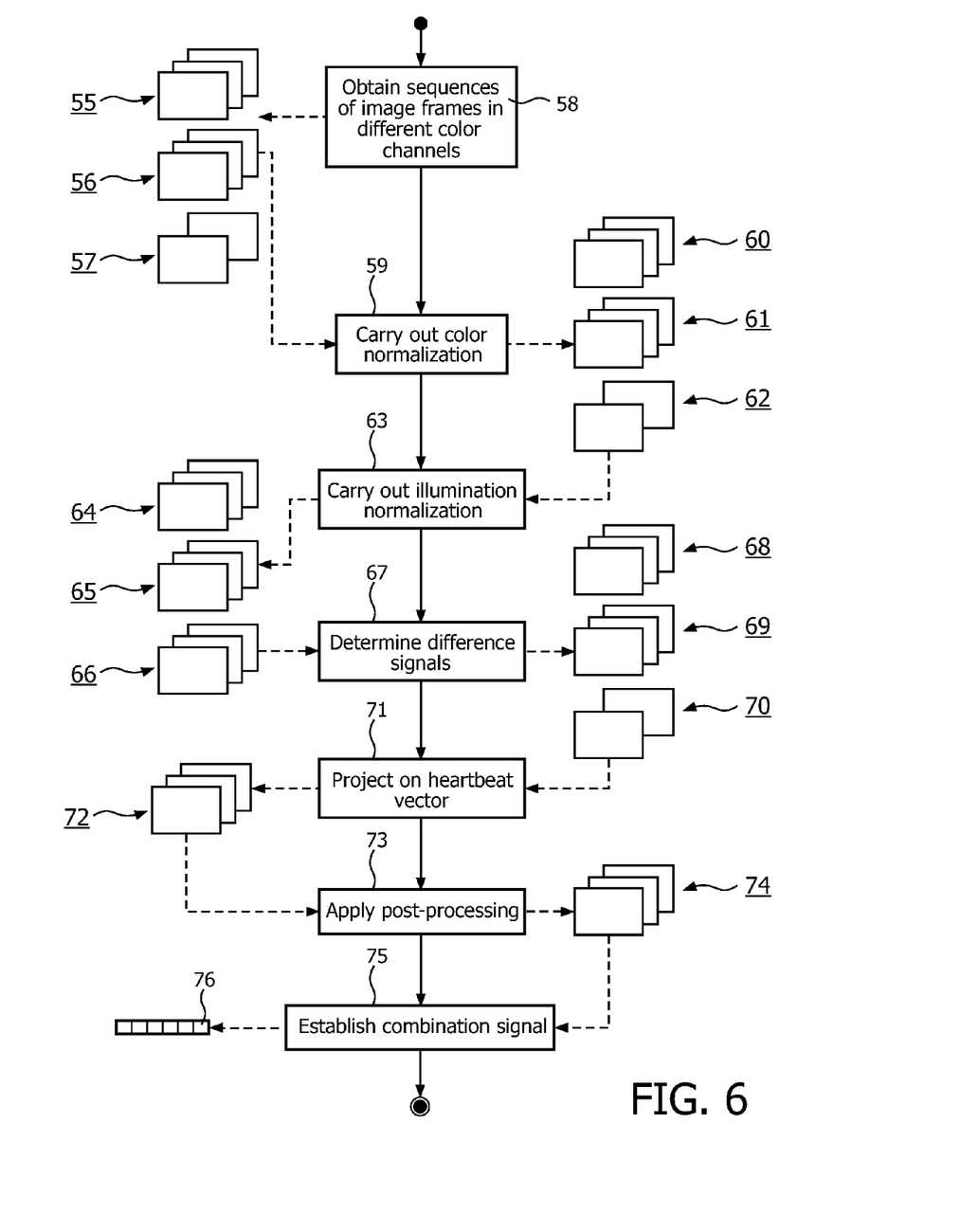
FIG. 6 is a flow chart illustrating an alternative method of obtaining a first signal for analysis to characterize at least one periodic component thereof.

A further embodiment of a method of carrying out remote photoplethysmography is illustrated in FIG. 6. This method can be regarded as an alternative to the method of FIG. 2, and is likewise carried out by the data processing system 1.

This method also takes as input a plurality of sequences 55-57 of image frames in respective color channels, corresponding to the sequences 18-20 illustrated in FIG. 2 and discussed above. Each image frame is comprised of pixel values representative of intensities of captured electromagnetic radiation in a frequency range associated with the sequence 55-57 concerned, a different respective frequency range being associated with each of the sequences 55-57. The sequences 55-57 are synchronized, in that a particular point in time corresponds to one image frame of each sequence 55-57. Each sequence 55-57 thus forms a signal, also referred to as a second signal herein. The image frames correspond to images of at least one living being, preferably a human being, with exposed skin. In the following detailed explanation, it will be assumed that complete image frames are processed, but the method of FIG. 6 can also be carried out on one or more tracked regions of interest, each the result of a segmentation operation aimed at identifying parts of the image frames representing exposed skin.

The sequences 55-57 of images frames are obtained in a first step 58, after which they are processed in parallel. That is to say that each forms an input to a respective sequence of at least one operation. At least one operation in each sequence involves the application of a factor of which the value is based on at least one value calculated on the basis of pixel values from the images frames in the sequences 55-57 themselves. These factors determine the relative influences of at least components of the sequences 55-57 on a final signal that is used to extract heart rate or respiration rate information (in a photoplethysmography application).

In the illustrated embodiment, color normalization (step 59) is carried out first, but the order of the operations in the sequence of operations can in principle be different. The color normalization step 59 is carried out to normalize the average skin tone within a time interval, and thus to eliminate the effects of slow changes in the illumination spectrum and of slow changes in the average skin tone due to motion. Motion can lead to changes in the average skin tone when pixels representing skin are imperfectly tracked. It can also lead to changes in the average skin tone when the environment in which the depicted subject moves is not illuminated uniformly, e.g. due to the presence of multiple light sources with different spectra or to colored reflective surfaces.

The color normalization step 59 in effect transforms the color space defined by the camera 7 to a normalized color space in which slow color changes have no effect. An effect of this normalization is (ideally) to provide a vector in a normalized color space that moves in parallel to a fixed line representative of color changes due to blood volume pulsations (the "heartbeat line").

Assuming that the sequences 55-57 of image frames correspond to Red, Green and Blue color channels, one can write the color change $\vec{H}_c(\vec{x},t)$ registered by the camera 7 at a pixel position $\vec{x}$ and point in time t as follows:

$$\vec{H}_c(\vec{x}, t) = \frac{d\vec{I}_c(\vec{x}, t)}{dt} = \frac{d}{dt} \begin{bmatrix} R_c(\vec{x}, t) \\ G_c(\vec{x}, t) \\ B_c(\vec{x}, t) \end{bmatrix} \quad (3)$$

The change in color due to varying blood volume (the phenomenon of interest in the case of remote photoplethysmography) is modulated by the local skin tone of the skin covering the blood volume and by the illumination sources. This is a multiplicative process, so that appropriate normalization will lead to demodulation.

The color normalization step 59 includes dividing the instantaneous color components by the corresponding time-average of the red, green and blue values. Instead of the average, a different combination of multiple values associated with respective different points in time spanning the point in time associated with the point in time for which the combination is being calculated could be taken. An example is the median value. The result of the color normalization step 59 is formed by three parallel sequences 60-62 of color-normalized images. The operation can be written as follows:

$$\vec{I}_n(\vec{x}, t) = \begin{bmatrix} R_n(\vec{x}, t) \\ G_n(\vec{x}, t) \\ B_n(\vec{x}, t) \end{bmatrix} = \begin{bmatrix} \frac{R_c(\vec{x}, t)}{\overline{R}_c(t)} \\ \frac{G_c(\vec{x}, t)}{\overline{G}_c(t)} \\ \frac{B_c(\vec{x}, t)}{\overline{B}_c(t)} \end{bmatrix}, \quad (4)$$

wherein $\vec{I}_n(\vec{x},t)$ is a normalized color vector, and $\overline{R}_c(t)$, $\overline{G}_c(t)$, $\overline{B}_c(t)$ are time-varying factors calculated separately for each of the parallel sequences 55-57 of image frames.

In one alternative variant to the one discussed herein, separate factor values $\overline{R}_c(\vec{x},t), \overline{G}_c(\vec{x},t), \overline{B}_c(\vec{x},t)$ are calculated and applied for each pixel position (i.e. there is no spatial combination).

In the illustrated variant, the factors $\overline{R}_c(t), \overline{G}_c(t), \overline{B}_c(t)$ are calculated on the basis of pixel values at multiple pixel positions within each of one or more regions of interest, and applied to pixels associated with positions within this region of interest. Thus, they can be written as follows:

$$\overline{R}_c(t) = \frac{1}{2\varepsilon|X|} \int_{t-\varepsilon}^{t+\varepsilon} \int_X R_c(\vec{x}, z) d\vec{x} dz, \quad (5)$$

$$\overline{G}_c(t) = \frac{1}{2\varepsilon|X|} \int_{t-\varepsilon}^{t+\varepsilon} \int_X G_c(\vec{x}, z) d\vec{x} dz,$$

and $$\overline{B}_c(t) = \frac{1}{2\varepsilon|X|} \int_{t-\varepsilon}^{t+\varepsilon} \int_X B_c(\vec{x}, z) d\vec{x} dz,$$

wherein |X| corresponds to the area of the region of interest X.

Of course, the data processing device 2 will process time-discrete signals. Although the average over time can use pixel values from more than two points in time, a simple and relatively accurate approximation uses pixel values from two successive points in time. One of these can correspond to the point in time for which the factor value is being calculated. In one example of an implementation of such a step, this can be written as:

$$I_{n,d}(x, t) = \frac{I_{c,d}(\vec{x}, t)}{I_{c,d}(\vec{x}, t) + I_{c,d}(\vec{x}, t-1)}. \quad (6)$$

Note that the region of interest corresponds to one single pixel position in this variant.

The color normalization step 59 should result in image frames of which the values of the pixels obey a Gaussian distribution. In a variant, those pixels with outlying values are not used to obtain a final signal (also referred to as "first signal" herein) for analysis to characterise at least one periodic component thereof. Additionally or alternatively, the method is applied iteratively. After color normalization, a region with the most stable distribution of pixel values over time is used as region of interest. Alternatively, the largest region could be used. In both alternatives, the fact that image parts representing exposed skin of a single living being should have a Gaussian distribution is used to segment the image frames. A color normalization factor appropriate to one of these segments is calculated and applied to pixel values associated with pixel positions in only that segment.

As illustrated in FIG. 6, the sequences 60-62 of color-normalized images undergo further processing in a next step 63, in which illumination normalization is carried out. It is noted that this step 63 can precede the color normalization step 59, and that one of these two normalization steps 59,63 can be omitted in some variants.

The illumination normalization step 63 takes account of the near impossibility of accurately tracking pixels through the sequences 55-57 of images, although it should generally be possible to segment out all those pixels representing exposed skin. However, variations in illumination strength and transmission of the skin will still show up when individual pixels are not tracked perfectly. Illumination normalization helps remove these effects. It also helps remove changes in brightness that are due to movement, rather than pulsating blood flow of the subject shown in the images.

The illumination normalization step 63 results in three further normalized sequences 64-66 of images. It can be represented mathematically as follows:

$$\vec{I}_b(\vec{x}, t) = \frac{1}{\alpha R_n(\vec{x}, t) + \beta G_n(\vec{x}, t) + \gamma B_n(\vec{x}, t)} \vec{I}_n(\vec{x}, t) \quad (7)$$

The parameters $\alpha$, $\beta$, $\gamma$ can have any value. Indeed, one or two of them can have the value zero. However, there is theoretically an optimum choice of values, which is that combination that causes the resulting normalized pixels to lie in a plane parallel to the heartbeat line in the normalized color space. In one embodiment, an analysis is carried out in order to select optimized values of the parameters $\alpha$, $\beta$, $\gamma$.

In a subsequent step 67 of the illustrated method, difference signals are established by subtracting from each current pixel value the value at the corresponding pixel position at the immediately preceding point in time, resulting in three sequences 68-70 of frames of difference values. It is noted that this step 67 can be combined with, for example, the color-normalization step 59, so that Equation (6) is modified to:

$$H_{n,d}(x, t) = \frac{I_{c,d}(\vec{x}, t) - I_{c,d}(\vec{x}, t - 1)}{I_{c,d}(\vec{x}, t) + I_{c,d}(\vec{x}, t - 1)} \quad (8)$$

The illustrated step 67 is the last in the parallel sequences of operations taking the sequences 55-57 of image frames (the "second signals") as input.

There follows a further step 71, in which an operation is carried out that combines normalized difference signals into a single signal of which each value is based on values from the respective normalized difference signals at corresponding points in time. In the illustrated embodiment, this step 71 involves a projection onto a line in the normalized color space that corresponds to color variations due to the pulsating blood flow of a living being. Any noise orthogonal to this line is eliminated in this step 71, which results in a single sequence 72 of frames. In a variant, outliers are also eliminated in this step 71.

Then, an optional post-processing step 73 is applied. This step 73 can involve such operations as bandpass filtering. The result is a sequence 74 of post-processed image frames.

Finally (step 75), at least one combination signal 76 is established. This signal is based on signals at multiple pixel positions, the result of processing them to obtain a consensus value. This step 75 can involve clustering, averaging, determining a median value, further outlier removal, and the like. This step 75 results in a stronger signal with a better signal-to-noise ratio. Fourier analysis can be applied to characterize at least one periodic component, e.g. the periodic component corresponding to the heartbeat signal or respiration signal.

In an alternative embodiment, the post-processing step 73 already involves a transformation from the time domain to the frequency domain.

The effect of the embodiments described above is to enable images captured with a relatively uncomplicated and inexpensive camera 7 to be used to characterize periodic phenomena that results in almost imperceptible colour variations in regions of interest within the image frames. The characterization is relatively reliable, because variations due to other influences are eliminated or at least suppressed.

It should be noted that the above-mentioned embodiments illustrate, rather than limit, the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The mere fact that certain measures are recited in mutually different dependent claims does not indicate that a combination of these measures cannot be used to advantage.

An embodiment in which both the video camera 7 and the sensors 9-11 are used is also possible, for example. Another embodiment in which a further camera is used in addition to the video camera 7 is also possible. For example, a thermal camera can provide a signal in one channel with the video camera 7 providing a signal in another channel.

The invention claimed is:

1. A method of facilitating obtaining a first signal for analysis to characterize at least one periodic component thereof, including acts of:
    obtaining at least two second signals representative of intensities of captured electromagnetic radiation, each corresponding to a respective different radiation frequency range,
    the first signal being at least derivable an output signal obtainable by applying a transformation to the second signals such that any value of the output signal is based on values from each respective second signal at corresponding points in time; and
    obtaining at least one value of at least one variable determining influences of at least components of respective second signals on the output signal when the signals corresponding to the second signals are captured and the transformation is applied, by at least one of:
    (i) analyzing at least one of the second signals, an output signal obtained by applying the transformation to the second signals and a first signal derived from the output signal and using the analysis to select at least one value of at least one parameter corresponding to a respective one of the variables; and
    (ii) calculating values of at least one time-varying factor corresponding to a respective one of the variables, each factor value based on at least one second signal value, and applying each factor in an operation in at least one of number of parallel sequences of operations comprising at least one such operation and taking a signal corresponding to a respective one of the second signals as input.

2. The method according to claim 1, wherein the analysis of at least one of the second signals, an output signal obtained by applying the transformation to the second signals and a first signal derived from the output signal is used to select at least one value of at least one parameter determining influences of at least components of respective second signals on the output signal so as to maximize a relative signal strength in a limited part of a spectrum of the first signal.

3. The method according to claim 1, wherein the transformation includes an operation carried out in parallel on respective input signals, each a different linear combination of second signals with at least one coefficient differing from zero, the operation comprising taking a logarithm of the input signal.

4. The method according to claim 1, wherein the analysis includes carrying out a principal component analysis on data sets respectively based on a plurality of second signals.

5. The method according to claim 1, wherein at least one of the second signals, an output signal obtained by applying the transformation to the second signals and a first signal derived from the output signal is analyzed and the analysis is used to select at least one value of at least one parameter determining influences of at least components or respective second signals on the output signal when the signals corresponding to the second signals are captured and the transformation is applied, the method further including causing the selected values of the at least one parameter to be loaded into a system comprising:
- an interface for obtaining at least two second signals representative of intensities of captured electromagnetic radiation, each corresponding to a respective different radiation frequency range; and
- a signal processing system for applying a transformation to the second signals to obtain an output signal from which the first signal is at least derivable, any value of the output signal being based on values from each respective second signal at a common point in time,
- wherein the system is arranged to cause influences of respective second signals on the output signal to be determined at least partly in accordance with the loaded values of the at least one parameter.

6. The method according to claim 1, wherein the analysis of at least one of the second signals, an output signal obtained by applying the transformation to the second signals and a first signal derived from the output signal and the selection of at least one parameter value is carried out continually whilst processing the second signals to obtain the first signal.

7. The method according to claim 1, wherein the at least one time-varying factor includes a factor obtainable by calculating a linear combination of corresponding values from each of at least one of the second signals, and wherein the same value of that factor is used in each of the parallel sequences of operations.

8. The method according to claim 1, wherein, for at least one of the factors, separate values at corresponding associated points in time are calculated for each of the parallel sequences, each obtained from multiple values of the second signal taken as input by the sequence concerned, the multiple values being associated with respective points in time spanning an interval including the point in time associated with the factor value.

9. The method according to claim 1, wherein the transformation includes at least one parameterized operation, and wherein the analysis of at least one of the second signals, an output signal obtained by applying the transformation to the second signals and a first signal derived from the output signal is used to select values of at least one parameter of the operation.

10. The method according to claim 9, wherein the operation is an operation taking at least two inputs based in different ways the second signals.

11. The method according to claim 9, wherein the transformation includes an operation carried out in parallel on respective input signals using at least one parameter value specific to fewer than all of the input signals.

12. The method according to claim 9, wherein the transformation includes at least one parameterized non-linear operation, and wherein the analysis of at least one of the second signals, an output signal obtained by applying the transformation to the second signals and a first signal derived from the output signal is used to select values of at least one parameter of the operation.

13. A system for obtaining a first signal for analysis to characterize at least one periodic component thereof, the system comprising a processor and a memory coupled to the processor, wherein the processor is configured to:
- obtain at least two second signals representative of intensities of captured electromagnetic radiation, each corresponding to a respective different radiation frequency range,
- the first signal being at least derivable from an output signal obtainable by applying a transformation to the second signals such that any value of the output signal is based on values from each respective second signal at corresponding points in time; and
- obtain at least one value of at least one variable determining influences of at least components of respective second signals on the output signal when the signals corresponding to the second signals are captured and the transformation is applied, by at least one of:
  (i) analyzing at least one of the second signals, the output signal and the first signal and using the analysis to select at least one value of at least one parameter corresponding to a respective one of the variables and determining influences of at least components of respective second signals on the output signal when signals corresponding to the second signals are captured and the transformation is applied; and
  (ii) calculating values of at least one time-varying factor corresponding to a respective one of the variables, each factor value based on at least one second signal value, and applying each factor in an operation at least one of a number of parallel sequences of operations comprising at least one such operation and taking a signal corresponding to a respective one of the second signals as input.

14. A non-transitory computer readable medium comprising computer instructions which, when executed by a processor, configure the processor to perform a method of facilitating obtaining a first signal for analysis to characterize at least one periodic component thereof, the method comprising acts of:
- obtaining at least two second signals representative of intensities of captured electromagnetic radiation, each corresponding to a respective different radiation frequency range, the first signal being at least derivable from an output signal obtainable by applying a transformation to the second signals such that any value of the output signal is based on values from each respective second signal at corresponding points in time; and
- obtaining at least one value of at least one variable determining influences of at least components of respective second signals on the output signal when the signals corresponding to the second signals are captured and the transformation is applied, by at least one of:
  (i) analyzing at least one of the second signals, an output signal obtained by applying the transformation to the second signals and a first signal derived from the output signal and using the analysis to select at least one value of at least one parameter corresponding to a respective one of the variables; and
  (ii) calculating values of at least one time-varying factor corresponding to a respective one of the variables, each factor value based on at least one second signal value, and applying each factor in an operation in at least one of a number of parallel sequences of operations comprising at least one such operation and taking a signal corresponding to a respective one of the second signals as input.

* * * * *